United States Patent [19]

Kimura et al.

[11] Patent Number: 5,186,839
[45] Date of Patent: Feb. 16, 1993

[54] SYRINGE TYPE COLUMN FOR CHROMATOGRAPHY

[75] Inventors: Masaru Kimura, Okayama; Hiromi Kochi, Fukuyama, both of Japan

[73] Assignee: Manac Inc., Hiroshima, Japan

[21] Appl. No.: 764,974

[22] Filed: Sep. 23, 1991

Related U.S. Application Data

[63] Continuation of Ser. No. 459,828, Jan. 26, 1990, abandoned.

[30] Foreign Application Priority Data

Jun. 3, 1988 [WO] World Int. Prop. O. ......... 88/00539

[51] Int. Cl.$^5$ .............................................. B01D 15/08
[52] U.S. Cl. .................................. 210/656; 210/198.2; 604/190
[58] Field of Search ...................... 210/635, 656, 198.2, 210/416.1, 472; 604/187, 190; 128/218; 436/161, 178; 422/70, 100, 101

[56] References Cited

U.S. PATENT DOCUMENTS

| | | | |
|---|---|---|---|
| 3,493,503 | 2/1970 | Mass | 604/190 |
| 3,810,545 | 5/1974 | Filz | 210/198.2 |
| 3,859,999 | 1/1975 | Ishikawa | 604/190 |
| 3,902,849 | 9/1975 | Barak | 210/198.2 |
| 3,976,529 | 8/1976 | Weischelbaum | 604/190 |
| 4,008,718 | 2/1977 | Pitesky | 604/190 |
| 4,061,143 | 12/1977 | Ishikawa | 604/190 |
| 4,168,147 | 9/1979 | Acuff | 436/161 |
| 4,214,993 | 7/1980 | Forsythe | 210/198.2 |
| 4,238,197 | 12/1980 | Eisentraut | 436/178 |
| 4,270,921 | 6/1981 | Graas | 210/198.2 |
| 4,341,635 | 7/1982 | Golias | 210/198.2 |
| 4,448,206 | 5/1984 | Martell | 604/190 |
| 4,572,210 | 2/1986 | McKinnon | 604/190 |
| 4,596,561 | 6/1986 | Meyer | 604/190 |
| 4,660,569 | 4/1987 | Etherington | 604/190 |
| 4,732,162 | 3/1988 | Martell | 604/190 |
| 4,787,971 | 11/1988 | Donald | 210/198.2 |
| 4,820,276 | 4/1989 | Moreno | 604/190 |
| 4,891,133 | 1/1990 | Colvin | 210/198.2 |
| 4,892,710 | 1/1990 | Wong | 436/178 |
| 4,936,315 | 6/1990 | Lineback | 128/765 |
| 4,973,450 | 11/1990 | Schulter | 436/178 |

FOREIGN PATENT DOCUMENTS

57-158553 9/1982 Japan ................................. 210/198.2

OTHER PUBLICATIONS

Abstract of Japan Patent No. 57-158553, Sep. 1982, 1 P 165.

Primary Examiner—Ernest G. Therkorn
Attorney, Agent, or Firm—Frishauf, Holtz, Goodman & Woodward

[57] ABSTRACT

A syringe type column used for liquid chromatography, wherein a stationary phase (4) and a solvent for development (5) are placed in a cylindrical barrel (1), and an air vent (2a) extends through a plunger (2) which is inserted in the barrel. Development is effected, while the air vent (2a) is closed to prevent air leakage therethrough, by pushing down the plunger (2). When the plunger (2) is drawn out in order to supplement the solvent for development, air flows into the cylindrical barrel (1) through the air vent (2a) so that an inner space of the barrel (1) is not held under a negative pressure and the stationary phase (4) is not disturbed.

10 Claims, 2 Drawing Sheets

SYRINGE TYPE COLUMN FOR CHROMATOGRAPHY

This application is a continuation of application Ser. No. 07/459,828, filed Jan. 26, 1990, now abandoned.

BACKGROUND OF THE INVENTION

This invention relates to a syringe type column to be used for chromatography, and more particularly to a syringe type column having a novel structure, in which the uniformity in a stationary phase filled in a column may not be disturbed even after repeating operations of introducing a solvent for development thereto, so that the stationary phase filled in the column may not be disorganized or disturbed even after performing operations where high separating efficiency are required.

With recently required precision of chemical reactions, development of simple and convenient methods for purifying or separating a trace of a reaction product is becoming desideratum. As one of such methods, there has been contemplated a pressurized chromatography technique applied with a medium pressure in which a syringe is used as a column. In this method, a barrel of the syringe having a discharge port at the tip is first filled with a silica gel granule, an alumina granule or a cellulose fiber, to which a predetermined amount of a solution containing the reaction product to be separated is then introduced, and further a predetermined amount of a solvent for development. Subsequently, a plunger is inserted in the barrel to be pressed thereinto gradually to effect development and separation of a desired object, which is sampled from the discharge port of the barrel.

When high separating efficiency is tried to be obtained using this method, the following inconvenience occurs.

For the purification or separation of the reaction product, it is generally necessary to introduce the solvent for development repeatedly to the stationary phase while uniformly maintaining it in the filled state. However, in the above method, the plunger must be drawn out of the barrel every time the solvent for development is introduced into the barrel. When the plunger is drawn out of the barrel, an inner space of the barrel inevitably suffers a negative pressure, so that the air flows into the barrel through the discharge port at the tip thereof, and the filled state of the stationary phase is subject to turbulence due to the movement of the air flowing into the barrel to break down an equilibrium state formed therein.

It is an object of this invention to provide a syringe-type column having a structure in which the solvent for development can repeatedly be introduced into the column while the equilibrium state formed in the stationary phase is maintained and without causing the inconvenience as described above in said repeated introduction of the solvent for development.

SUMMARY OF THE INVENTION

The syringe type column of this invention comprises a cylindrical barrel having a solution discharge port at one end and an opening at the other end; and a plunger which is inserted from the open end of the cylindrical barrel and has at least one air vent formed to extend therethrough along the direction of an axis thereof.

DETAILED DESCRIPTION

Figure 2:
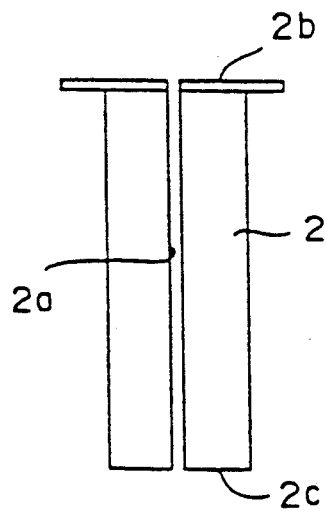
FIG. 2 shows, in longitudinal cross-section, a plunger which is the other member of the column of this invention.
Figure 1:
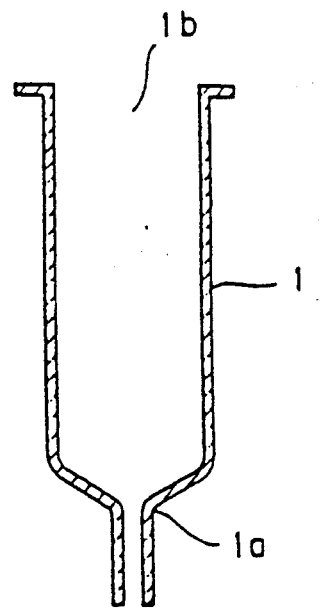
FIG. 1 shows, in longitudinal cross-section, a cylindrical barrel which is one member of the column of this invention.

The column of this invention will now be described in more detail referring to the drawings. FIG. 1 and FIG. 2 show, in longitudinal cross-section, the cylindrical barrel and the plunger, respectively, which constitute a column when they are combined with each other.

The cylindrical barrel 1 has, on the whole, for example, a cylindrical shape, wherein the solution discharge port 1a is provided at a bottom end and wherein an upper end is defined as the open end 1b. The plunger 2 has at least one air vent 2a formed to pierce or extend therethrough along the longitudinal axis thereof from an upper surface 2b to a lower surface 2c.

Figure 3:
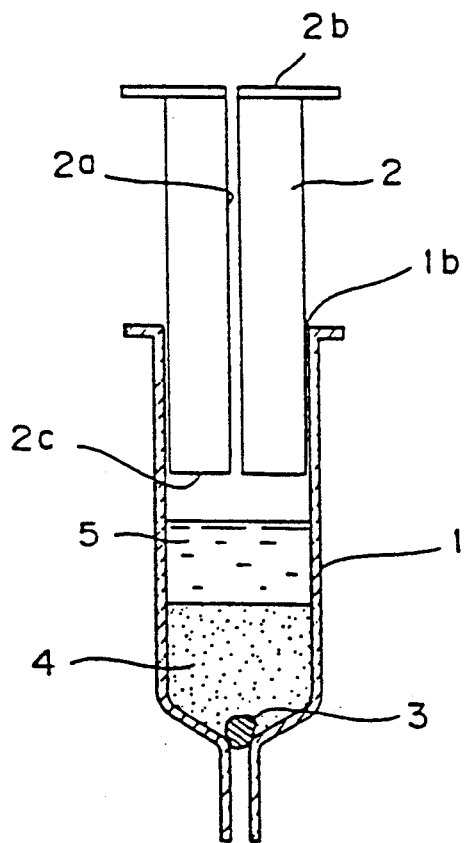
FIG. 3 is an illustration for explaining the operation of the column of this invention.

The column of this invention is operated as follows: As shown in FIG. 3, the outlet of the solution discharge port 1a of the cylindrical barrel 1 is sealed with a liquid-permeable member 3 such as cotton. Next, a predetermined amount of a stationary phase 4 is filled into the barrel 1. As the stationary phase 4, a suitable one may be selected depending on the purpose from those used for ordinary column chromatography and HPLC. Subsequently, a predetermined amount of sample solution is introduced from the open end 1b and then a predetermined amount of a solvent for development 5 is further introduced.

The plunger 2 is then inserted in the open end 1b to be pressed into the barrel 1 with finger pressure of an operator being applied to the upper surface 2b thereof.

As the plunger 2 is pressed into the barrel 1, the solvent for development 5 permeates through the stationary phase 4, whereby a desired object can gradually be eluted. When the lower surface 2c of the plunger 2 substantially comes into abutment against an upper surface of the stationary phase 4 after consumption of the solvent for development 5, the finger applied to the upper surface 2b of the plunger 2 is released to draw out the plunger 2.

In the above drawing-out process, air flows into the barrel 1 through the air vent 2a, so that an inner space of the barrel 1 will never suffer negative pressure. Moreover, since the air flows in not through the solution discharge port 1a but through the air vent 2a of the plunger 2, the stationary phase 4 will never be subject to turbulence due to the movement of the in-flowing air.

Figure 4:
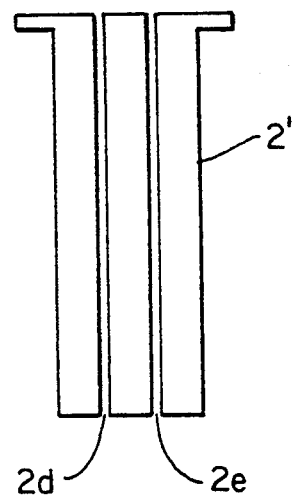
FIG. 4 shows another embodiment of the plunger of this invention.

FIG. 4 shows another embodiment of the plunger 2' in which two air vents 2d and 2e are formed to pierce or extend therethrough. In the plunger 2' of this embodiment, the solvent for development 5 can be introduced into the barrel 1 through the other air vent 2e without drawing out the plunger 2' therefrom.

The cylindrical barrels 1 and plungers 2, 2' may be made of glass or a resin such as polyethylene.

As is apparent from the above description, the column of this invention has very high practical value, since the solvent for development 5 can be introduced thereinto repeatedly without breaking down the equilibrium state formed in the stationary phase 4 to thereby obtain high efficiency of separating the desired object.

We claim:

1. A method of using a column for use in liquid chromatography, using a generally cylindrical barrel having a solution discharge port at one end thereof and an opening at another end thereof, the method comprising:

closing said solution discharge port with a liquid-permeable member;

filling a predetermined amount of a stationary phase into said barrel;

introducing a predetermined amount of a sample solution through said opening of said barrel;

introducing a predetermined amount of a solvent for development into said barrel;

inserting a plunger into said opening of said barrel, said plunger having at least one air vent formed therein and which extends therethrough in the longitudinal direction thereof;

pressing said plunger into the interior of said barrel by finger pressure thereon to cause said solvent for development to permeate through said stationary phase;

releasing said finger pressure, withdrawing said plunger from said barrel so that air flows into said barrel, from the outside, not through said solution discharge port but through said at least one air vent to prevent negative pressure in said barrel, whereby said stationary phase is never subjected to turbulence due to the movement of the in-flowing air and introducing of additional solvent for development into said barrel; and repeating said last three steps in order for a predetermined number of times.

2. The method of claim 1, wherein said plunger has an outer surface portion in sliding sealing contact with inner walls of said barrel so as to seal against said inner walls of said barrel when said plunger is pressed into and withdrawn from said barrel.

3. The method of claim 2, wherein said plunger has at least two vents extending therethrough from one end surface to an opposite end surface thereof, and wherein the method comprises introducing said solvent for development through one of said vents.

4. The method of claim 1, comprising closing said at least one air vent while applying said finger pressure to press said plunger into said barrel.

5. The method of claim 1, wherein said plunger has at least two vents extending therethrough from one end surface to an opposite end surface thereof, and wherein the method comprises introducing said solvent for development through one of said vents.

6. A method of using a column for use in liquid chromatography, using a generally cylindrical barrel having a solution discharge port at one end thereof and an opening at another end thereof, the method comprising:

(a) closing said solution discharge port with a liquid-permeable member;

(b) filling a predetermined amount of a stationary phase into said barrel;

(c) introducing a predetermined amount of a sample solution through said opening of said barrel;

(d) introducing a predetermined amount of a solvent for development into said barrel;

(e) inserting a plunger into said opening of said barrel, said plunger having at least two vents formed therein and which extend therethrough in the longitudinal direction thereof;

(f) pressing said plunger into the interior of said barrel by finger pressure thereon to cause said solvent for development to permeate through said stationary phase;

(g) releasing said finger pressure and introducing additional solvent for development through one of said vents;

(h) permitting air to flow into said barrel, from the outside, not through said solution discharge port but through the other of said vents to prevent disturbing of the stationary phase in said barrel, whereby said stationary phase is never subjected to turbulence due to the movement of the in-flowing air; and (i) repeating said steps (f), (g) and (h) in order for a predetermined number of times.

7. The method of claim 6, wherein said plunger has an outer surface portion in sliding sealing contact with inner walls of said barrel so as to seal against said inner walls of said barrel when said plunger is pressed into and withdrawn from said barrel.

8. The method of claim 6, comprising closing said at least two vents with a finger while applying said finger pressure to press said plunger into said barrel.

9. The method of claim 6, comprising introducing said additional solvent for development through said one of said vents without withdrawing said plunger from said barrel.

10. The method of claim 6, comprising closing said at least two vents while applying said finger pressure to press said plunger into said barrel.

* * * * *